(12) United States Patent
van der Maas et al.

(10) Patent No.: US 7,258,840 B2
(45) Date of Patent: Aug. 21, 2007

(54) SAMPLE VIAL WITH TRANSPONDER

(75) Inventors: Marinus Frans van der Maas, Arnemuiden (NL); Joachim Dieter P. Gerstel, Mulheim (DE)

(73) Assignees: SGT Exploitatie B.V., Moers (DE); Joint Analytical Systems GmbH, Moers (DE)

( * ) Notice: Subject to any disclaimer, the term of this patent is extended or adjusted under 35 U.S.C. 154(b) by 771 days.

(21) Appl. No.: 10/381,771

(22) PCT Filed: Oct. 1, 2001

(86) PCT No.: PCT/NL01/00715

§ 371 (c)(1),
(2), (4) Date: Jan. 20, 2004

(87) PCT Pub. No.: WO02/26385

PCT Pub. Date: Apr. 4, 2002

(65) Prior Publication Data

US 2004/0152202 A1 Aug. 5, 2004

(30) Foreign Application Priority Data

Sep. 29, 2000 (NL) .................................... 1016298

(51) Int. Cl.
*B01L 3/00* (2006.01)
*B01L 3/14* (2006.01)
(52) U.S. Cl. .................. 422/102; 436/164; 422/68.1; 422/913; 340/572.1; 340/572.8; 340/10.51; 235/375
(58) Field of Classification Search .......... 422/99, 422/61, 62–67, 68.1, 913, 103, 104, 915, 422/917, 102; 340/572.1, 540, 505, 539.1, 340/10.1, 5.2, 10.51, 572.8; 700/231, 245, 700/266; 436/164, 43–48, 180; 235/375, 235/487, 492
See application file for complete search history.

(56) References Cited

U.S. PATENT DOCUMENTS

| | | | | |
|---|---|---|---|---|
| 3,613,955 A | * | 10/1971 | Wetherell, Jr. | ................ 222/83 |
| 4,248,355 A | * | 2/1981 | Kolb et al. | .................. 215/274 |
| 6,066,299 A | * | 5/2000 | Lodge | ......................... 422/102 |
| 6,475,443 B1 | * | 11/2002 | van Deursen et al. | ...... 422/102 |
| 6,652,812 B1 | * | 11/2003 | Vartiainen et al. | .......... 422/102 |
| 7,091,864 B2 | * | 8/2006 | Veitch et al. | ............. 340/572.8 |

FOREIGN PATENT DOCUMENTS

| | | |
|---|---|---|
| DE | 299 15 334 U | 12/1999 |
| EP | 0 875 292 A1 | 11/1998 |
| WO | WO99 03585 A | 1/1999 |

\* cited by examiner

*Primary Examiner*—Walter Griffin
*Assistant Examiner*—Imran Akram
(74) *Attorney, Agent, or Firm*—Weingarten, Schurgin, Gagnebin & Lebovici LLP

(57) ABSTRACT

Vial comprising an outer vial and an inner vial, wherein in the space enclosed between the inner vial and the outer vial a memory chip is included, characterized in that the inner vial and outer vial are connected to each other with the aid of a connecting ring, such that they are detachable from each other, the connecting ring forming a seal in that this can only be broken by destruction, the memory chip being connected to the outer vial. The invention also relates to a method for the use of a vial for the purpose of performing an analysis on a sample and to a system for practicing the method using vials according to the invention.

24 Claims, 1 Drawing Sheet

SAMPLE VIAL WITH TRANSPONDER

Figure 1:
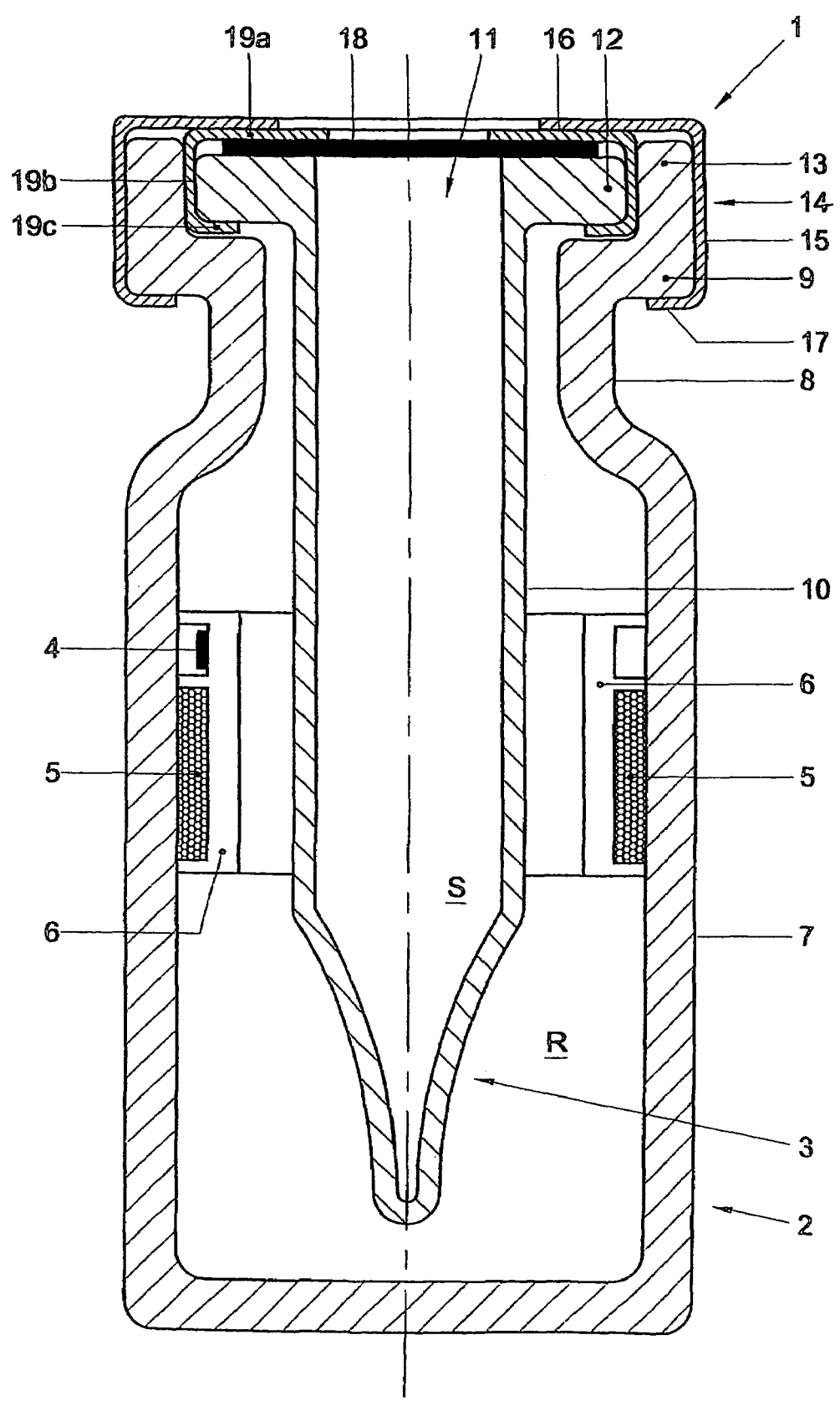

The invention relates to a vial provided with an outer vial and an inner vial, wherein, in the space enclosed by the inner vial and the outer vial, a memory chip is included.

Such a vial is known from FIG. 2 of the European patent application EP-A-0 875 292. It is known that vials are disposable products. It is therefore highly important to the customers that the price of a vial be low. Heretofore, the vial known from the European patent application has been too expensive to be used in practice, notably because the entire vial, the memory chip included, has to be thrown away after use. To the present day, the prices of the memory chips do not allow this. As is known from the European patent application mentioned, it is of great importance that, during use, the sample cannot be separated from the memory chip, so that confusion of data stored relative to a particular sample in a particular memory chip, with data of another sample cannot occur. Such confusion has indeed always been completely precluded with the known vial, however, as indicated hereinabove, the use of the known vial was so costly that, up to the present day, this has impeded its introduction in practice.

The invention contemplates a vial, the use of which is considerably less expensive than the known vial, while it is still guaranteed that the data of a particular sample which are stored in a memory chip of a vial, are never confused with the data of another sample. Hence, a vial with which no fraud can be committed and which meets the standards set by the various government, agencies, such as, for instance, the Food and Drug Administration, more in particular FDA21CFRL11, the Environmental Protection Agency, and with the aid of which the requirements can be met which are set by Good Laboratory Practice (GLP), Good Manufacturing Practice (GMP) and/or Standard Operation Practice (SOP).

To this end, the vial of the type described in the preamble is characterized according to the invention in that the inner vial and the outer vial are connected to each other with the aid of a connecting ring, so that they are detachable from each other, the connecting ring forming a seal in that it can only be broken by destruction, the memory chip being connected to the outer vial, the inner vial being provided with an inner vial cap, which comprises a top wall with a central opening, a side wall contiguous with the top wall, while a lower edge of the side wall is folded around a lower side of a collar of the inner vial, a filling opening of the inner vial being provided with a septum for closure thereof, the septum being enclosed between the top wall of the inner vial cap and a top wall of the inner vial collar.

Such a vial is relatively inexpensive in use in that the outer vial with the memory chip can be used over and over again and only the inner vial needs to be replaced after use. After analysis of the sample present in the inner vial, the inner vial can be separated from the outer vial and a new inner vial can be placed in the outer vial. Such recycling can take place in the laboratory itself, but can also take place in a recycling facility, especially equipped to that end Such a recycling facility can, for instance, be set up by the producer of the vials according to the invention.

According to a further elaboration of the invention, the connecting ring can have a substantially cap-shaped configuration with a side wall and a top wall, a lower edge of the side wall being folded around a collar of the outer vial, while the inner vial is enclosed between the collar of the outer vial and the top wall of the connecting ring. The top wall of the connecting ring can be provided with an opening, so that the interior of the inner vial is accessible. Optionally, the filling opening of the inner vial can be provided with a septum for closure thereof. Then, evidently, this septum closes off the opening in the top wall of the connecting ring.

When a sample is to be brought into or taken out of the inner vial, the septum is pierced with a needle, with the aid of which the sample can be added or removed, respectively. Such a septum is known per se and the skilled person knows the operation thereof.

According to a further elaboration of the invention, in the space enclosed between the inner vial and the outer vial, further an antenna can be included, which is connected to the memory chip to form a transponder. With such a transponder, the memory of the memory chip can be written on and/or read out remotely.

According to an alternative, further elaboration of the invention, the memory chip can also be provided with contact points or proximity sensors, arranged for exchanging information by direct or virtually direct contact between the memory chip and read/write equipment.

The invention also relates to a method for the use of a vial for performing an analysis on a sample. The object of the method is to enable the performance of an analysis using a vial provided with a memory chip such as, for instance, a transponder, while the costs of the use of such a chip still remain limited. To that end, the method according to the invention comprises the following steps:

providing a vial according to the invention;

placing a sample in the inner vial;

storing an identification, coupled to the sample, in the memory chip of the vial;

analysing the sample;

storing the analysis data of the respective sample;

after storage of the analysis data, breaking the connecting ring and separating the outer vial and the inner vial.

When storing the analysis data, these analysis data are coupled to the identification mentioned. Storing the analysis data can take place in the memory chip of the vial but also in a laboratory information management system (LIMS) or like database. However, the analysis data should always be coupled to the unique identification of the sample. As the connecting ring is only broken after storage of the analysis data and the outer vial is separated from the inner vial, it is prevented that an identification of a sample, stored in the memory chip of the vial in which the sample is present, will, at any given time, inadvertently, or as the result of fraud, be coupled to a different sample. The fact is that sample and identification are coupled to each other until after storage of the analysis. This coupling is physical with the aid of a connecting ring serving as a seal. When the coupling is broken this is visible as the connecting ring has to be destroyed to that end.

According to a further elaboration of the invention, the method can further comprise at least one pre-analytic step, such as centrifuging, weighing or the like.

According to a further elaboration of the invention, it is preferred that after breaking the connecting ring and separating the outer vial and the inner vial, a new inner vial is placed in the outer vial. Also, at that moment, or afterwards, the memory of the memory chip can be erased.

Optionally, the memory chip can be loaded with the various pre-analytical and analytical operations the sample has to undergo, the pre-analytical and analytical processing stations being provided with read/write devices for reading out information from and writing information in the memory chip.

The various pre-analytical and analytical processing stations can be provided with control software and displays, the displays providing information to the user about the operations to follow, depending on the information coming from the memory chip of the respective vial. Besides providing information, the control software of the processing stations can be designed such that it prevents execution of an operation which is not programmed in the memory chip, and gives directions to the user about the operation which does have to be performed.

Further, the invention relates to a system for practising the method according to the invention using vials according to the invention, the system comprising at least a number of processing stations for performing an operation on a sample present in a vial, at least one of the processing stations being provided with a read/write station for, respectively, reading out information from the memory chip of a vial and writing information in the memory chip of a vial, the system being provided with a control provided with control software arranged for processing the information coming from the memory chip.

Such a system offers the advantage that the analysis can be carried out without confusion of samples while, still, use is made of vials with a memory chip, such as for instance a transponder.

According to a further elaboration of the invention, it is preferred that the various processing stations are provided with displays, the software providing the system user, via the displays, with information about the operations to be performed, which a particular vial has to undergo. Such a system can even be operated by relatively unskilled analysts without this lack of training leading to incorrect pre-analytical and analytical operations.

Optionally, the various processing stations can even be controlled by the control such, that these processing stations perform the operation dictated by the control, suitable for the respective sample at the respective processing station.

It will be clear that the processing stations can comprise pre-analytical processing stations, such as, for instance, centrifuges and weighing devices, and analytical processing systems, such as, for instance, gas chromatographs and mass spectrographs, all known per se.

Hereinbelow, the invention will be elucidated on the basis of two exemplary embodiments of vials according to the invention which can be used with the method according to the invention and in the system according to the invention.

FIG. 1 shows a cross sectional view of a first exemplary embodiment of a vial.

FIG. 1 show a vial 1, which are provided with an outer vial 2, and an inner vial 3. In the space R enclosed by the outer vial 2 and the inner vial 3, a memory chip 4 is included. In the present exemplary embodiments, this memory chip 4 is connected to an antenna 5 designed as a coil. More in particular, the combination shown of the memory chip 4 with antenna 5 is a transponder whose memory can be loaded with data and be read out remotely. It is clearly visible that the memory chip 4 and the antenna 5 are connected to the outer vial. To that end, they are both embedded in a plastic layer 6, which, in the present exemplary embodiments, is designed as a cylindrical ring 6, connected with an outer surface to the inner wall of the outer vial 2. It is noted that instead of or in addition to the antenna 5, the memory chip 4 can be provided with contact points or proximity sensors arranged for exchanging information by direct contact or virtually direct contact between the memory chip and the read/write equipment. In the present exemplary embodiments, the inner vial 3 is a disposable and the outer vial 2 with memory chip 4 is reusable by fitting a new inner vial 3 therein.

In the present exemplary embodiment, the outer vial 2 comprises a substantially cylindrical body 7, provided at the top with a neck-shaped constriction 8. The constriction 8 links up with an outer vial collar 9. The inner vial 3 comprises a substantially cylindrical body 10 with a filling opening 11 at one end. The body 10 of the inner vial 3 bounds an inner space S, which serves for receiving a sample. At the filling opening 11, the inner vial 3 is provided with an inner vial collar 12. In a fitted condition, the inner vial collar 12 rests on the outer vial collar 9. In both exemplary embodiments, the outer vial collar 9 links up with a cylindrical wall 13 whose inner diameter is such that the inner vial collar 12 is receivable therein.

The outer vial 2 is connected with the inner vial 3 with the aid of a connecting ring 14, such that they are mutually detachable, the connecting ring 14 forming a seal in that this can only be broken by destruction. The connecting ring 14 has a substantially cap-shaped configuration with a side wall 15 and a top wall 16. A lower edge 17 of the side wall 15 is folded around the collar 9 of the outer vial 2. The inner vial 3 is enclosed between the collar 9 of the outer vial 2 and the top wall of the connecting ring 16. In both exemplary embodiments, the top wall 16 of the connecting ring 14 is provided with a central opening which gives access to the filling opening 11 of the inner vial 3. In the present exemplary embodiments, the connecting ring 14 is designed in aluminum. Aluminum offers the advantage that it can be easily folded with the aid of a hand tool. Moreover, removing an aluminum connecting ring 14 is not particularly complicated. The vials 1, generally designed in glass, undergo the removal of a connecting ring 14 without these vials 1, thereby sustaining damage. Upon removal of the connecting ring 14, the connecting ring 14 itself, however, is irreparably damaged.

The exemplary embodiment is further provided with a septum 18.

In the exemplary embodiment the inner vial 3 is provided with an inner vial cap 19, which comprises a top wall 19a with a central opening, a side wall-19b contiguous to the top wall 19a, while a lower edge 19c of the side wall 19b is folded around a lower side of the inner vial collar 9. The septum is enclosed between the top wall 19a of the inner vial cap 19 and a top wall of the inner vial collar 12. This inner vial 3, in itself closed off by a connecting cap 19 and a septum 18 is connected to the outer vial 2 with the aid of the connecting ring 14.

To ensure a clearance-free connection between the inner vial and the outer vial, between the collar of the inner vial and the collar of the outer vial a distance ring may be included. This distance ring can be designed in aluminum, plastic or rubber.

For the method of the use of the vial or the analysing system in which the vial can be applied, reference is made to the introduction to the specification of the present application.

It will be clear that the invention is not limited to the exemplary embodiments described but that various modifications within the framework of the invention are possible.

The invention claimed is:

1. A vial comprising an outer vial and an inner vial, wherein, in the space enclosed by the inner vial and the outer vial, a memory chip is included, characterized in that the inner vial and outer vial are connected to each other with the aid of a connecting ring such that they are detachable from each other, the connecting ring forming a seal in that it can only be broken by destruction, the memory chip being connected to the outer vial, the inner vial being provided with an inner vial cap, which comprises a top wall with a central opening, a side wall contiguous to the top wall, while a lower edge of the side wall is folded around a lower side of a collar of the inner vial, a filling opening of the inner vial being provided with a septum for closure thereof, the septum being enclosed between the top wall of the inner vial cap and a top wall of the inner vial collar.

2. A vial according to claim 1, characterized in that the connecting ring has a substantially cap-shaped configuration with a side wall and a top wall, a lower edge of the side wall being folded around a collar of the outer vial, the inner vial being enclosed between the collar of the outer vial and the top wall of the connecting ring.

3. A vial according to claim 2, characterized in that the top wall of the connecting ring is provided with an opening.

4. A vial according to claim 2, characterized in that the outer vial has a cylindrical body, provided at a top side with a neck-shaped constriction, this constriction linking up with said outer vial collar, the inner vial having a substantially cylindrical body with a filling opening at one end, the substantially cylindrical body of the inner vial bounding an inner space (S) which serves for receiving a sample, the inner vial, at the filling opening thereof, being provided with said inner vial collar, while, in a fitted condition, the inner vial collar rests on the outer vial collar.

5. A vial according to at least claim 4, characterized in that to the outer vial collar, an upstanding cylindrical wall is contiguous whose inner diameter is such that the inner vial collar is receivable therein.

6. A vial according to claim 1, characterized in that the connecting ring is manufactured from aluminum.

7. A vial according to claim 1, characterized in that the inner vial cap is manufactured from aluminum.

8. A vial according to claim 1, characterized in that in the space (R) enclosed between the inner vial and the outer vial further an antenna is included, which is connected to the memory chip to form a transponder.

9. A vial according to claim 1, characterized in that the memory chip is provided with contact points or approximation sensors arranged for exchanging information by direct contact or virtually direct contact between the memory chip and read/write equipment.

10. A vial according to claim 1, characterized in that the inner vial is a disposable and the outer vial with memory chip is re-usable by fitting a new inner vial therein.

11. A method for the use of a vial for the purpose of performing an analysis on a sample, comprising the following steps:
providing a vial according to claim 1;
placing a sample in the inner vial;
storing an identification, coupled to the sample, in the memory chip of the vial;
analysing the sample;
storing the analysis data of the respective sample;
after storing the analysis data, breaking the connecting ring and separating the inner vial and the outer vial.

12. A method according to claim 11, characterized in that it further comprises at least one pre-analytical step, such as centrifuging, weighing or the like.

13. A method according to claim 11, characterized in that, after breaking the connecting ring and separating the outer vial and the inner vial, a new inner vial is placed in the outer vial.

14. A method according to claim 13, characterized in that at or after separation of the outer vial and the inner vial, the memory of the memory chip is erased.

15. A method according to claim 11, characterized in that the memory chip is further loaded with the various pre-analytical and analytical operations the sample has to undergo, the pre-analytical and analytical processing stations being provided with read/write-devices for reading out information from and writing information in the memory chip.

16. A method according to claim 15, characterized in that the various pre-analytical and analytical processing stations are provided with control software and displays, the displays providing information to the user about the operations to follow depending on the information coming from the memory chip of the relevant vial.

17. A method according to claim 16, characterized in that the control software of the processing stations, besides providing information, is further arranged such that it prevents the execution of an operation not programmed in the memory chip and gives directions to the user as to the operation which does have to be performed.

18. A system for practicing the method of claim 11 comprising an outer vial and an inner vial, wherein, in the space enclosed by the inner vial and the outer vial, a memory chip is included, characterized in that the inner vial and outer vial are connected to each other with the aid of a connecting ring such that they are detachable from each other, the connecting ring forming a seal in that it can only be broken by destruction, the memory chip being connected to the outer vial, the inner vial being provided with an inner vial cap, which comprises a top wall with a central opening, a side wall contiguous to the top wall, while a lower edge of the side wall is folded around a lower side of a collar of the inner vial, a filling opening of the inner vial being provided with a septum for closure thereof, the septum being enclosed between the top wall of the inner vial cap and a top wall of the inner vial collar;

and further comprising at least a number of processing stations for performing an operation on a sample present in a vial, at least one of the processing stations being provided with a read/write station for, respectively, reading information from the memory chip of a vial and writing information in the memory chip of a vial, the system being provided with a control provided with software arranged for processing the information coming from the memory chip.

19. A system according to claim 18, characterized in that the processing stations are provided with displays, the software providing the system user via the displays with information about the operations to be performed which a particular vial is to undergo.

20. A system according to claim 19, characterized in that the processing stations are controlled by the control such that they perform the process prescribed by the control, suitable for the relevant sample at the relevant processing station.

21. A vial according to claim 3, characterized in that the outer vial has a cylindrical body, provided at a top side with a neck-shaped constriction, this constriction linking up with said outer vial collar, the inner vial having a substantially cylindrical body with a filling opening at one end, the substantially cylindrical body of the inner vial bounding an inner space (S) which serves for receiving a sample, the inner vial, at the filling opening thereof, being provided with said inner vial collar, while, in a fitted condition, the inner vial collar rests on the outer vial collar.

22. A vial according to claim 5, characterized in that:
the connecting ring is manufactured from aluminum;
the inner vial cap is manufactured from aluminum;
either in the space (R) enclosed between the inner vial and the outer vial further an antenna is included, which is connected to the memory chip to form a transponder; or the memory chip is provided with contact points or approximation sensors arranged for exchanging information by direct contact or virtually direct contact between the memory chip and read/write equipment;
the inner vial is a disposable and the outer vial with memory chip is re-usable by fitting a new inner vial therein.

23. A method according to claim 12, characterized in that:
after breaking the connecting ring and separating the outer vial and the inner vial, a new inner vial is placed in the outer vial;
at or after separation of the outer vial and the inner vial, the memory of the memory chip is erased;
the memory chip is further loaded with the pre-analytical and analytical operations the sample has to undergo, the pre-analytical and analytical processing stations being provided with read/write-devices for reading out information from and writing information in the memory chip;
the various pre-analytical and analytical processing stations are provided with control software and displays, the displays providing information to the user about the operations to follow depending on the information coming from the memory chip of the relevant vial; and
the control software of the processing stations, besides providing information, is further arranged such that it prevents the execution of an operation not programmed in the memory chip and gives directions to the user as to the operation which does have to be performed.

24. A method for the use of a vial for the purpose of performing an analysis on a sample, comprising the following steps:
providing a vial according to claim 22;
placing a sample in the inner vial;
storing an identification, coupled to the sample, in the memory chip of the vial;
analysing the sample;
storing the analysis data of the respective sample;
after storing the analysis data, breaking the connecting ring and separating the inner vial and the outer vial.

* * * * *

UNITED STATES PATENT AND TRADEMARK OFFICE
CERTIFICATE OF CORRECTION

| | | |
|---|---|---|
| PATENT NO. | : 7,258,840 B2 | Page 1 of 1 |
| APPLICATION NO. | : 10/381771 | |
| DATED | : August 21, 2007 | |
| INVENTOR(S) | : Marinus Frans Van der Maas et al. | |

It is certified that error appears in the above-identified patent and that said Letters Patent is hereby corrected as shown below:

On the Title Page, Item (75) Inventors, "Arnemuiden" should read --Arnernuiden--; and Column 1, line 32, "FDA21CFRL11" should read --FDA21CFR11--.

Signed and Sealed this

Twenty-seventh Day of January, 2009

JOHN DOLL
*Acting Director of the United States Patent and Trademark Office*